United States Patent [19]

Bjornson

[11] 4,097,997

[45] Jul. 4, 1978

[54] X-RAY CALIPERS

[76] Inventor: Allen L. Bjornson, 5746 Preston View Blvd., #1006, Dallas, Tex. 75240

[21] Appl. No.: 677,145

[22] Filed: Apr. 15, 1976

[51] Int. Cl.² .......................... G06G 1/02; G01B 5/06; A61B 5/10
[52] U.S. Cl. .................................. 33/1 SD; 33/143 C; 33/148 E; 128/2 S; 235/88 R
[58] Field of Search .............. 33/1 SD, 143 C, 148 E, 33/149 R, 174 D; 128/2 R, 2 A, 2 S; 235/61 R, 61 A, 78 R, 88 R, 116

[56] References Cited

U.S. PATENT DOCUMENTS

| | | | |
|---|---|---|---|
| 2,533,580 | 12/1950 | Hall | 235/88 R |
| 2,663,086 | 12/1953 | Gardner | 33/148 E |
| 3,058,653 | 10/1962 | Des Granges | 235/88 R |
| 3,333,343 | 8/1967 | Elfast, Jr. | 33/149 R |
| 3,604,622 | 9/1971 | Yamada | 235/78 R |

FOREIGN PATENT DOCUMENTS

| | | | |
|---|---|---|---|
| 1,279,282 | 10/1968 | Fed. Rep. of Germany | 33/149 R |
| 355,634 | 7/1961 | Switzerland | 33/1 SD |

*Primary Examiner*—Richard E. Aegerter
*Assistant Examiner*—Richard R. Stearns

[57] ABSTRACT

An X-ray caliper is disclosed having upper, intermediate, and lower discs movable relative to each other, the upper and lower discs have arms extending therefrom between which the part of the anatomy to be x-rayed is positioned, the upper disc has a chart thereon of electrical current versus time and the intermediate disc has on the top surface thereof scales of peak kilovoltages and on the lower surface thereof a listing of various parts of the anatomy. When the part of the anatomy to be x-rayed has been measured and that part listed on the intermediate disc has been positioned relative to the lower disc, the peak kilovoltage range will appear opposite the chart on the upper disc and values of time, electrical current and the product thereof for various kilovoltages can be read therefrom for setting an x-ray machine. The chart can also be moved relative to the upper disc.

13 Claims, 7 Drawing Figures

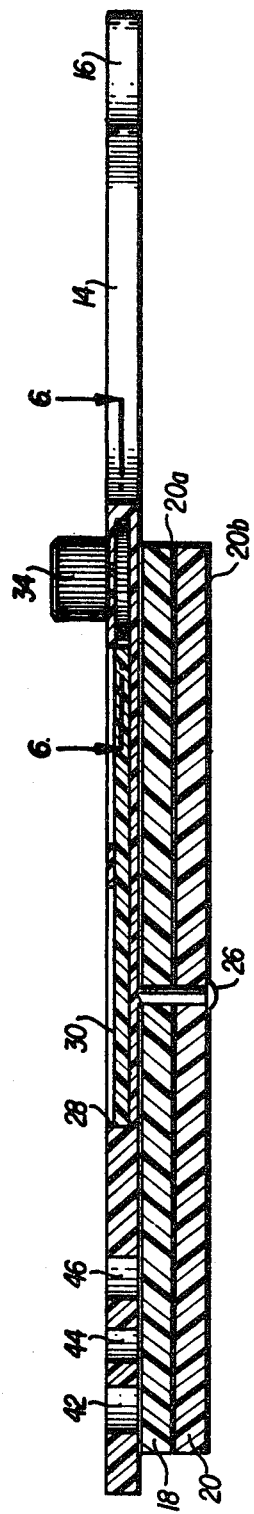

X-RAY CALIPERS

BACKGROUND OF THE INVENTION

1. Field of the Invention

This invention relates to x-ray calipers and more particularly to a caliper from which, upon measuring by and setting on the caliper the part of the anatomy to be x-rayed, the proper value of milliampere-seconds (MAS) can be determined for a desired peak kilovoltage value related to either the chest or extremities of the anatomy or the Bucky technique.

Discussion of the Prior Art

Applicant is unaware of any caliper in existence of similar construction or capable of performing the functions of the caliper of the present invention. Devices of which applicant is aware fall generally into two categories, namely, those which are merely capable of measuring the part of the human anatomy to be x-rayed and nothing more such as that disclosed in U.S. Pat. No. 3,213,541 to H. L. Roffman and those which are merely technique charts giving setting information for an x-ray machine after the part of the anatomy to be x-rayed has been measured by a separate instrument and numerous variables have been decided upon by the radiologist or x-ray technician. Inasmuch as the experience and judgement as well as personal x-ray taking technique varies considerably between operators, the overall quality and other characteristics of an exposure taken of the same part of the anatomy by several different operators using the same technique charts will often itself vary considerably. This not only makes proper diagnosis difficult but may in some instances result in overexposure of the patient to x-rays causing destruction of tissue, somatic effects, or genetic effects in the patient's offspring.

Thus, there is a great need for an x-ray caliper which is both capable of measuring all parts of the body capable of being x-rayed and which gives the correct technical exposure factors for that measurement irregardless of the part of the body being x-rayed or technical changes the operator wishes to introduce.

SUMMARY OF THE INVENTION AND OBJECTS

This invention is a device for measuring any part of the human anatomy capable of being x-rayed and for determining the correct technical exposure factors for that particular part of the anatomy measured. Factors related to a particular or combination of techniques an also be easily introduced during operation of the device.

Incorporated in the device is the standard increase of two kilovolts for each centimeter increase in measurement of the part of the anatomy to be x-rayed which pertains to what is well known in the art as the "variable kilovoltage technique." However, more importantly, the device is also designed so that the "optimum kilo voltage technique" can be practiced which results in uniform radiograph quality. This uniform quality is achieved through complete control and standardization of exposure procedures inasmuch as the x-ray taking apparatus, film and processing chemicals are substantially standardized already.

Briefly, the "optimum kilovoltage technique" as practiced with the device of the present invention is as follows. By trial, a fixed or optimum kilovoltage is established for an average tissue thickness range and for a given projection. Once it has been found that the kilovoltage selected produces the most desirable amount of penetration and contrast for the given human part, irrespective of size, it is established as a constant. The name of the body part is the printed on the device as a standard. This procedure is repeated for all of the parts of the body frequently x-rayed.

In use, the part of the body to be x-rayed is measured by caliper arms attached to an upper and lower dial of the device. An intermediate dial has on one surface thereof the aforementioned written parts of the body and the part measured is positioned in registry with a window on the lower dial. The other surface of the intermediate dial has three ranges of kilovoltages which appear in one of three windows adjacent a chart on the upper dial and which chart is of current in milliamperes versus time in fractions of a second and their product milliampere seconds or MAS. Inasmuch as the measurement of the part, its name and kilovoltage are now in direct proportion to each other, all that the operator need do is select one variable, the desired MAS value and the x-ray machine can be set. A dial is provided on the upper disc for moving the chart relative to the kilovoltage ranges appearing adjacent thereto to compensate or factor in various technical changes such as those required when screens, grids, cones, etc. are used.

It is therefore the primary object of the present invention to provide a device for measuring any part of the human anatomy capable of being measured and for determining the correct technical exposure factors for that particular part of the anatomy.

It is another object of the present invention to provide a device with which either variable or optimum kilovoltage technique can be used in determining the correct exposure factors for setting an x-ray machine.

It is still another object to provide an x-ray caliper which eliminates guess work by standardizing the exposure resulting in uniform, high quality radiographs.

It is yet another object to provide an x-ray caliper which is synchronized to the x-ray machine by means of a factor change dial so measurement and technique are directly related.

It is a further object to provide an x-ray caliper which is easy and fast to operate and which is relatively inexpensive to manufacture.

The foregoing and other objects and advantages will become apparent to those skilled in the art by referring to the following description and accompanying drawings, wherein:

FIG. 5 is a cross-sectional view taken along the lines 5—5 of FIG. 1;

FIG. 6 is a partial view in cross-section of the caliper taken along the lines 6—6 of FIG. 5; and FIG. 7 is a plan view of a part of the caliper showing an arm in its detached mode.

DETAILED DESCRIPTION OF THE INVENTION

Figure 1:
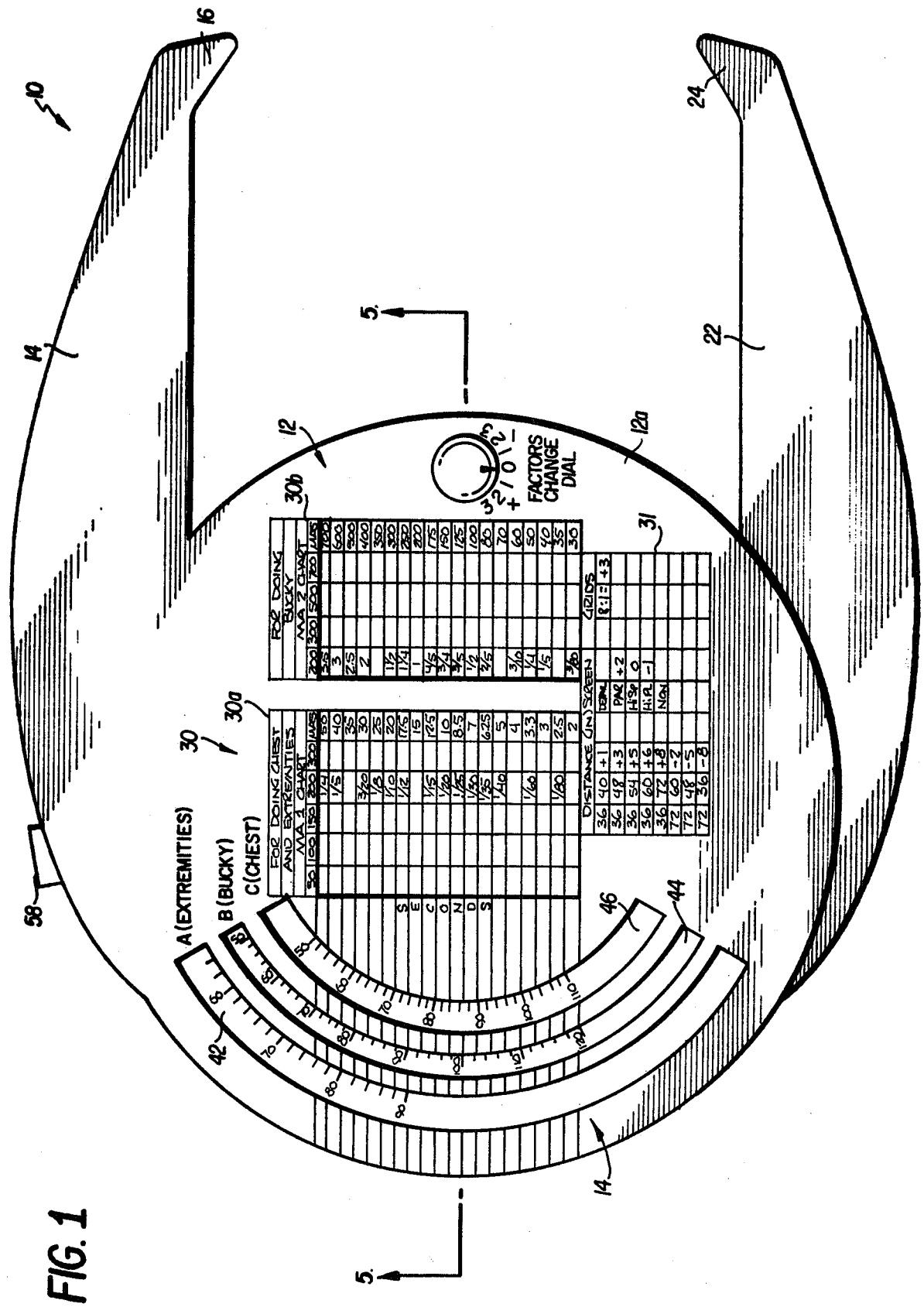
FIG. 1 is a plan view of the top side of the caliper of the present invention.
Figure 2:
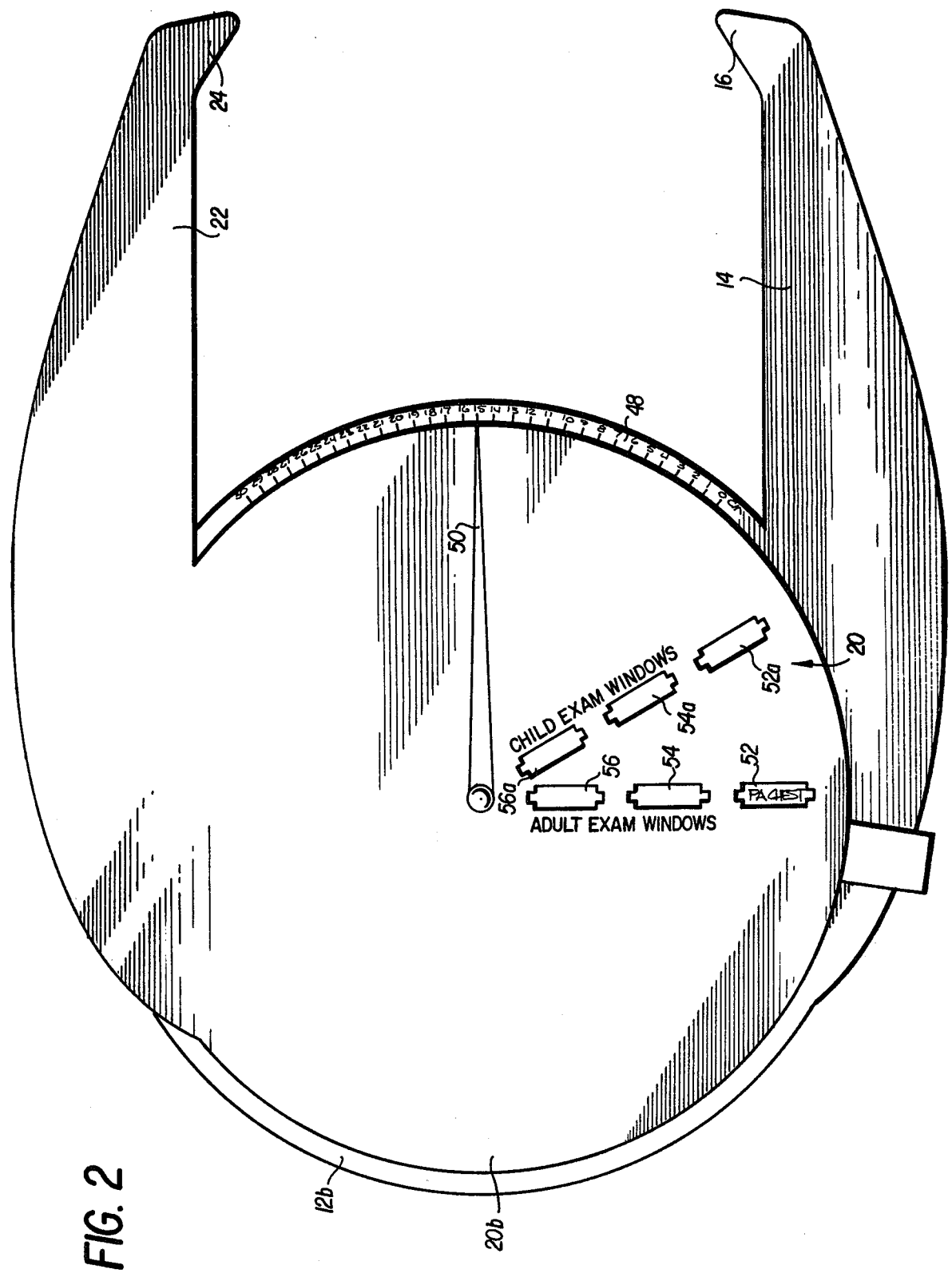
FIG. 2 is a plan view of the bottom side of the caliper of the present invention.

Referring now to the drawings where like characters of reference indicate similar elements in each of the several views, FIGS. 1 and 2 disclose at 10 applicant's novel caliper. The caliper 10 basically consists of an upper dial 12 in the form of a circular-shaped disc having an arm 14 extending therefrom and terminating in a projection 16, an intermediate circular shaped dial 18, and a lower dial 20 having an arm 22 extending therefrom and terminating in a projection 24 disposed opposite the projection 16 on arm 14. The dials 12, 18, 20 are made of plastic or other suitable rigid, lightweight material. The upper dial 12 has a top surface 12a and bottom surface 12b, intermediate dial 18 has a top surface 18a and a bottom surface 18b and lower dial 20 has a top surface 20a and a bottom surface 20b.

A pin 26 is secured at the center of upper dial 12 and extends outwardly a distance therefrom. Intermediate dial 18 and lower dial 20 are mounted at their respective centers on pin 26 so that all three dials are free to rotate relative to each other.

Upper dial 12 has a rectangular-shaped recess 28 formed therein and in which recess is slidably mounted a chart 30. The chart 30 has a row of gear teeth 32 formed along one end thereof as can best be seen by referring to FIGS. 5 and 6. A dial or knob 34 is also rotatably mounted on the upper dial 12 by means of a shaft 36 which in turn is connected to a gear 38 having teeth 40. The dial 34 is called the Factors Change Dial and has indicia formed on the top surface thereof as shown in FIG. 1. The operation of the Factors Change Dial will be discussed later. It is sufficient to say at this point that the teeth 40 of gear 38 are in meshing engagement with teeth 32 of chart 30 such that when the dial 34 is rotated one increment plus or minus, the chart 30 will move forward and backward one increment of time.

The chart 30 is divided into two segments, one segment 30a related to the Chest and Extremities of the body capable of being x-rayed and the other segment 30b is related to the well known Bucky radiographic technique. With few exceptions, the Bucky diaphragm or other grid should be used for radiographing of all parts of the anatomy twelve centimeters or more in thickness with the exception of the lungs, heart (except for large, heavy patients), lateral mandible hands, wrists, ankles, legs and sinuses. Each segment is divided into a plurality of stations across and each station is divided down. The stations across represent increments of current in milliamperes ranging, for example, from 50 to 300 milliamperes with the exception of the last station and the divisions of each station downward represent increments of decimals or time in fractions of a second ranging, for example, for one-fourth of a second to one-eightieth of a second. The last station represents the MAS or milliampere seconds which is the product of a particular value of milliamperes such as 200 times a particular value of time such one-tenth of a second for a product of 20 as shown on the Chest segment of chart 30, the same being true for the Bucky segment. For clarity, only one station of time values are shown on each segment.

The division lines of each time segment downward on chart 30 are extended to the left as viewed in FIG. 1 on top surface 12a and across three arcuate-shaped recesses or windows formed in upper dial 12. The first recess 42 is labeled A (Extremities), the second recess 44 is labeled B (Bucky) and the third recess 46 is labeled C (Chest) again for reasons which will be more fully explained later.

Printed beneath chart 30 for quick and ready reference are additional charts 31 for such factors as Distance, Screen, Grids, Filters, Age and Pathology, as examples. Beneath such factor headings are various values which are commonly called Change Factors in the art. Various values from the various factors can be used individually or combined to determine the amount the Factors Change Dial, dial 34 should be rotated as will also be more fully described later with reference to the operation of the device.

The bottom surface 12b of dial 12 has printed thereon a range of distances 48 in centimeters as can best be viewed in FIG. 2, for example, from 0 to 30 centimeters. The lower dial 20 has an indicator 50 printed on its lower surface 20b opposite the range of distances 48 such that when the projections 16, 24 are touching, the indicator 50 is in registry with 0 centimeters on the range of distances 48 and for each increment of 1 centimeter distance the projections 16, 24 are rotated apart, the sum of such increments will be indicated opposite indicator 50. The lower dial 20 also has a plurality of windows 52, 54 and 56 formed therethrough between surfaces 20a and 20b for viewing indicia printed on the bottom surface 18b of intermediate dial 18 again for reasons which will be more fully explained later.

Figure 4:
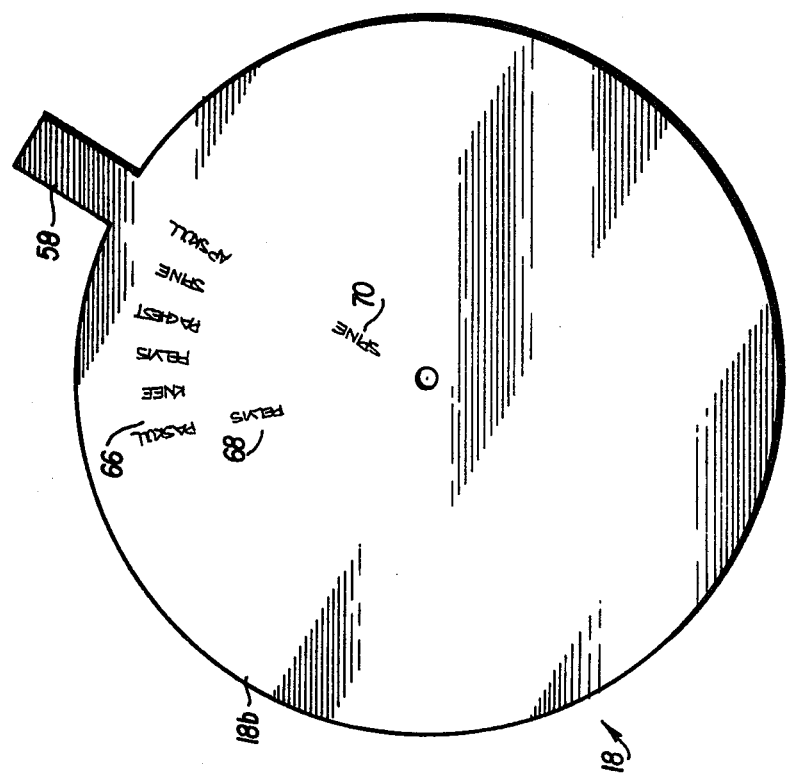
FIG. 4 is a plan view of the other side of the intermediate dial of the caliper.
Figure 3:
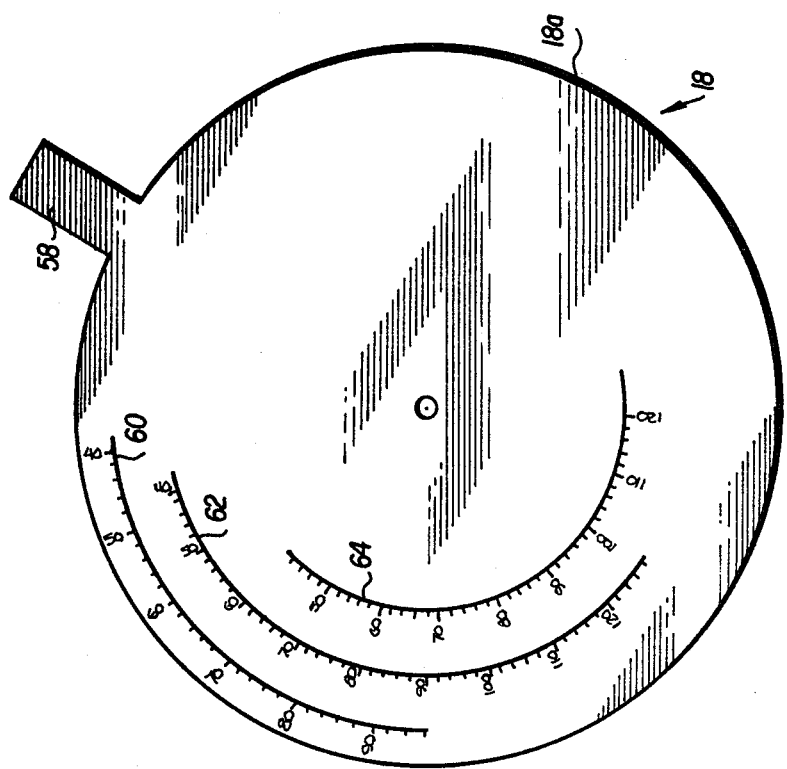
FIG. 3 is a plan view of one side of the intermediate dial of the caliper.

The intermediate dial 18 as can best be seen by referring to FIGS. 3 and 4 has an arm 58 integrally formed therewith which enables intermediate dial 18 to be manually moved relative to upper and lower dials 12, 20. The upper surface 18a has three ranges of peak kilovoltages (KVP) printed thereon in values from approximately 40 to 120 and are indicated by reference numerals 60, 62 and 64. Each kilovoltage range is divided into increments of 10 kilovolts and each increment of ten kilovolts is itself divided into five sub-increments of 2 kilovolts each. Thus, when any of the KVP ranges 60, 62, 64 are positioned in their respective windows 42, 44, 46 adjacent the chart segments 30a, 30b and intermediate dial 18 is held fixed relative to lower dial 20, a movement of one centimeter distance between projections 16, 24 will cause any of the KVP ranges to move exactly two kilovolts relative to a time increment on either chart 30a or 30b. In addition, in KVP range 60 (A Extremities) every increment of 10 KVP is equal to the width of 5 time increments on charts 30a, 30b, in KVP range 62 (B Bucky) every increment of 10 KVP is equal to the width of 4 time increments on charts 30a, 30b and in KVP range 64 (C Chest) every increment of 10 KVP is equal to the width of 3 time increments on charts 30a, 30b.

The lower surface 18b has formed thereon three arcuate rows 66, 68 and 70 within which various parts of the human anatomy capable of being x-rayed are listed (row 66) or where parts can be written in by the operator (rows 68, 70) for reasons that will be described later with reference to the operation of the device. More specifically, the parts of the anatomy appearing in row 66 have been printed in a certain position such that when the part is positioned in window 52 of lower dial 20, the proper range of kilovoltages will be brought into position in windows 42, 44 or 46 adjacent chart 30 as that part is being measured between projections 16, 24 or when the average known measurement for that part is lined up by indicator 50 adjacent centimeter range 48.

The windows 52, 54 and 56 would be used if the patient is an adult, however, if the patient is a child under twelve years of age, an additional set of windows 52a, 54a and 56a are provided. The child exam windows, when used, automatically result in a decrease in the kilovoltage (KVP) on side 18a of intermediate dial 18 when the range of voltages 60, 62 and 64 appear in windows 42, 44 and 46 for the various parts of the anatomy.

Referrring now to FIG. 7, another embodiment is shown wherein the arms 14 and 22 are removable. The arm 14 associated with the upper dial 12 only is shown for simplicity, it being understood that the lower arm 22 is of identical construction. The upper dial arm 14 in this embodiment has an arcuate projection 80 integrally formed therewith and with one or more holes 82 formed therethrough. The upper dial 12 has an arcuate groove 84 or recess formed in the periphery thereof slightly larger than projection 80 and it also has holes 86 formed in the upper and lower surfaces thereof. When the projection 80 is in position in groove 84, pins (not shown) can be used in the holes 82, 86 to secure the parts together and the device can function as a caliper. If the caliper feature is not required, the arms 14 and 22 can be removed and the distance measurement set by means of indicator 50 and centimeter range 48.

OPERATION

The general operation of the device will now be discussed together with the function of the Factors Change Dial.

As an example, suppose it is desired to take an x-ray of the chest of an adult patient from the posterior to the anterior side thereof. The patient's chest is measured between projections 16, 24 and say it measures, for example, 15 centimeters as indicated by indicator 50. Keeping the indicator on 15 centimeters, the intermediate dial 18 is then rotated so that the designation "PA Chest" appears in window 52. When "PA Chest" or any of the anatomical part names printed on side 18b appears in the window 52, the optimum KVP ranges are automatically set on side 18a for that part which is commonly referred to as the Optimum Kilovoltage Technique. The KVP ranges are thus set and never vary.

With all of the dials 12, 18, 20 held in this position, the chart 30a is viewed which pertains to the Chest and Other Extremities. The milliampere or MA stations start at 50 and go in increments of 50 to 300. Time settings have been indicated only under the 200 milliampere station for the sake of clarity as aforementioned and they determine how long to expose the patient. If 1/30 of a second is chosen as the time duration and the line therefrom to the left, as viewed in FIG. 1, leads to the KVP ranges, the KVP range C (Chest) would be chosen and the value 90 KVP would appear adjacent 1/30 of a second. To the right of 1/30 of a second, as viewed in FIG. 1 is a column of MAS values which are obtained by multiplying time by milliamperes or in this example 1/30 times 200 or approximately 7 MAS. The x-ray machine setting would be 90 KVP, 200 MA, 1/30 sec. Time or 90 KVP, 7 MAS.

As will be noted, 70 KVP lines up with 1/10 second (20 MAS) and 80 KVP lines up with 1/15 second (12.5 MAS) both of which are also good techniques for the same chest as are any other KVP values between 60 and 110 KVP, the operator only gains a faster or slower time speed by using them. Choosing a KVP value from a range of satisfactory values as just described is referred to in the art as the Milliampere-Seconds Kilovoltage Peak Computer.

It should be noted that if the chest had measured sixteen centimeters, this additional one centimeter would advance the KVP range by two KVP relative to the 1/30 time value. Thus, the KVP values are always advanced or reduced two KVP relative to a specific time for each change of one centimeter distance measured which is standard in the art. The use of the Factor Change Dial to modify the setting of the foregoing example will be discussed after consideration of the next example which pertains to the use of the caliper and the Optimum Voltage Technique.

If a new kilovoltage has been found by trail to be an optimum one for a specific body part and projection not shown on intermediate dial surface 18b, it can easily be added or incorporated into the device of the present invention by positioning the indicator 50 on the measurement of the part on centimeter range 48, the intermediate dial 18 is then rotated to position the optimum kilovoltage value obtained by trail opposite the MAS value obtained where it appears on chart 30. The name of the part is then written in either window 54 or 56. The kilovoltage, the measurement of the part, its name, and milliampere seconds are in direct proportion to each other. The exposure technique is thus standardized. If the part is classified as outside of the average thickness range — larger or smaller, refer to chart 31 for the correction factor.

The Factors Change Dial would be operated in the following manner with respect to the foregoing example wherein a patient's chest was to be x-rayed and the setting was initially determined from the device to be 90KVP and 1/30 of a second time duration of 7 MAS. If it was then deemed desirable to use an 8:1 grid, the Chart 31 is consulted and it indicates under the heading Grids that a positive three time step change is required. The Factors Change Dial would be rotated to the positive three position. This rotation will move the chart 30 downward three time steps so that now a time of 1/15 second appears opposite 90 KVP and the MAS is now 12.5. If it is then further desired to reduce the distance from 72 inches to 60 inches, the Distance heading is consulted which shows a minus two time step change required. The Factors Change Dial is rotated back two time steps from its plus three position which results in a net movement of one time step. The final setting to thus obtain a radiograph of identical quality after the change factors have been introduced as would have been obtained before such introduction would be 90 KVP, 1/25 of a second time duration and the MAS is 8.5.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. An x-ray caliper for use in measuring the part of the anatomy to be x-rayed and determining the proper voltage, current and time duration settings for an x-ray machine, said caliper comprising:

(a) upper, intermediate and lower dial means mounted for rotational movement relative to each other, said upper and lower dial means each having additional means associated therewith to enable said upper and lower dial means to be positioned relative to each other an amount from an initial position, said amount corresponding to the measured distance between opposite sides of said part of said anatomy to be x-rayed; and (b) indicia on one surface of said intermediate dial means indicating at least one range of operating voltages for said x-ray machine cooperating with chart means on said upper dial means for indicating desired x-ray machine operating values proportional to time as a function of said operating voltages, and indicia on the other surface of said intermediate dial means indicating at least two parts of the anatomy capable of being x-rayed cooperating with index means located on the lower surface of said lower dial means and arranged such that said chart means will indicate proper settings for said x-ray machine for the part of the anatomy indexed.

2. An x-ray caliper as set forth in claim 1 wherein said additional means comprises scale means on said upper dial means indicating increments of distance from an initial point and indicator means on said lower dial means opposite said scale means, said upper and lower dial means being in said initial position relative to each other when said indicator means is opposite said initial point on said scale means.

3. An x-ray caliper as set forth in claim 2 wherein said additional means further comprises upper and lower arm means connected respectfully at one end to said upper and lower dial means and wherein the free ends of said arms move relative to each other through an operating range as said upper and lower dial means are so moved.

4. An x-ray caliper as set forth in claim 3 wherein at least one of said ranges of operating voltages on said intermediate dial means is adjacent said chart means throughout said operating range of said upper and lower arms.

5. An x-ray caliper as set forth in claim 4 wherein said indicia on said one surface of said intermediate dial means comprises three separate ranges of operating voltages, one related to the chest portion of the anatomy, one related to the extremities of the anatomy and one related to the Bucky technique.

6. An x-ray caliper as set forth in claim 1 wherein said index means is at least one aperture formed through said lower dial means.

7. An x-ray caliper as set forth in claim 4 wherein said range of operating voltages is divided into increments of voltage and said chart is divided into increments of time.

8. An x-ray caliper as set forth in claim 4 wherein said upper dial means further comprises knob means mounted for rotation thereon and said chart means is movable relative to said upper dial means and operatively connected to said knob means such that the rotation of said knob means causes said relative movement of said chart means to thereby compensate for changes required by the use of screens, grids and the like.

9. An x-ray caliper as set forth in claim 8 wherein movement of one predetermined increment of rotation of said knob means will result in one predetermined increment of movement of said chart means relative to said upper dial means.

10. An x-ray caliper as set forth in claim 7 wherein said chart means is divided into increments of time versus increments of electrical current and the product of each of said increments of time and electrical current is also indicated on said chart.

11. An x-ray caliper as set forth in claim 10 wherein said chart is so divided such that if said product is multiplied by two, the resultant is indicated four increments of time from said product.

12. An x-ray caliper as set forth in claim 6 wherein said index means comprises at least two apertures through said lower disc means, said apertures being spaced from each other and equidistant from the center of said intermediate disc.

13. An x-ray caliper for use in measuring the part of the anatomy to be x-rayed and determining the proper voltage, current and time duration settings for an x-ray machine, said caliper comprising:
(a) upper, intermediate and lower dial means mounted for rotational movement relative to each other;
(b) said upper dial means having an arm thereon extending a distance therefrom, said upper dial means having a chart on the top surface thereof indicating values of time versus electrical current and a scale on the lower surface thereof indicating distance;
(c) said lower dial means having an arm thereon extending a distance therefrom said lower dial means having an indicator thereon disposed opposite said scale on said upper dial means such that the distance between the ends of said arms as said arms are moved relative to each other will be shown on said scale opposite said indicator, and
(d) said intermediate dial means having an upper surface with at least one scale thereon graduated in kilovoltages cooperating with said chart means on said upper dial means for indicating x-ray machine operating values proportional to time as a function of said kilovoltages and indicia on the other surface of said intermediate dial means indicating at least two parts of the anatomy capable of being x-rayed cooperating with index means located on the lower surface of said lower dial means and arranged such that said chart means will indicate proper settings for said x-ray machine for the part of the anatomy indexed.

* * * * *